(12) United States Patent
Blanchard

(10) Patent No.: US 7,745,163 B2
(45) Date of Patent: Jun. 29, 2010

(54) METHOD FOR IDENTIFYING ACETYLTRANSFERASE SUBSTRATES

(75) Inventor: John S. Blanchard, Pelham, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 683 days.

(21) Appl. No.: 10/574,307

(22) PCT Filed: Oct. 1, 2004

(86) PCT No.: PCT/US2004/032356

§ 371 (c)(1),
(2), (4) Date: Apr. 20, 2007

(87) PCT Pub. No.: WO2005/044077

PCT Pub. Date: May 19, 2005

(65) Prior Publication Data

US 2007/0269842 A1    Nov. 22, 2007

Related U.S. Application Data

(60) Provisional application No. 60/508,483, filed on Oct. 3, 2003.

(51) Int. Cl.
*C12Q 1/48* (2006.01)
(52) U.S. Cl. .......................... 435/15; 435/193
(58) Field of Classification Search .................. 435/15, 435/193
See application file for complete search history.

(56) References Cited

U.S. PATENT DOCUMENTS

| 5,869,275 A * | 2/1999 | Huang .......................... 435/15 |
| 6,225,074 B1 | 5/2001 | Wright et al. |
| 6,423,696 B1 | 7/2002 | Collins et al. |
| 2002/0002144 A1 * | 1/2002 | Klein et al. .................... 514/44 |

OTHER PUBLICATIONS

McCarthy A. et al. Reaction of Chloroacetyl CoA with Rabbit Fatty Acid Synthase. FEBS Letters 147(2)256-260, Oct. 1982.*
Tian W. et al. Affinity Labeling of Chicken Liver Fatty Acid Synthase with Chloroacetyl CoA and Bromopyruvate. Biochimica et Biophysica Acta 998(3)330-336, 1989.*
Patel S. et al. Substrate Specificity of Acetyl Coenzyme A Synthetase. J of Biological Chemistry 262(15)7132-7134, 1987.*
Davis J.T. et al., "Biosynthetic Thiolase from Zoogloea ramigera/II. Inactivation with Haloacetyl CoA Analogs"; J. Biol. Chem, 1987, vol. 262, No. 1, pp. 90-96.
Marcus A. and Elliott W.B., "Enzymatic Reactions of Fluoroacetyl Phosphate"; J. Biol. Chem., 1959, vol. 234, No. 5, pp. 1011-1014.
Polevoda B. and Sherman F., "N-terminal Acetyltransferases and Sequence Requirements for N-terminal Acetylation of Eukaryotic Proteins"; J. Mol. Biol., 2003, vol. 325, pp. 595-622.
Roth S.Y. et al, "Histone Acetyltransferases"; Annu. Rev. Biochem., 2001, vol. 70, pp. 81-120.

* cited by examiner

*Primary Examiner*—Ralph Gitomer
(74) *Attorney, Agent, or Firm*—Amster, Rothstein & Ebenstein LLP

(57) ABSTRACT

The present invention is directed to a method of identifying an acetyltransferase substrate in a sample that includes the steps of: (a) contacting the sample with (i) a reagent comprising a thiol-containing compound, a halo-acetyl-CoA or a halo-acetyl-pantetheine, and (ii) an acetyltransferase, under conditions suitable for acetyltransferase enzyme activity, and (b) identifying a substrate that has formed a base-stable covalent bond to the reagent, wherein the reagent is labeled with a label and/or the acetyltransferase is labeled with an affinity tag, and the substrate is the acetyltransferase substrate.

18 Claims, 7 Drawing Sheets

Chloroacetylation of histones by Hat1 Acetyltransferase

Comassie Staining

Chloroacetylation
50 mM Tris pH 7.3
200 µM ClAcetylCoA
9 µM histones (0.8 mg/ml)
0.4 µM Hat1 (0.02mg/ml)

Fluorometric Detection

Thiol capture
3 mM TAMRA-$CH_2CH_2SH$
200 mM pH 8.4 Tris
4 hr

METHOD FOR IDENTIFYING ACETYLTRANSFERASE SUBSTRATES

CROSS-REFERENCE TO RELATED APPLICATIONS

This is a U.S. National Phase of PCT Application No. PCT/US2004/032356, filed Oct. 1, 2004, which claims the benefit of U.S. Provisional Application No. 60/508,483, filed Oct. 3, 2003.

STATEMENT OF GOVERNMENT SUPPORT

This invention was made with U.S. Government Grant No. A133696 awarded by the National Institutes of Health. Accordingly, the United States government has certain rights in this invention.

BACKGROUND (1) Field of the Invention

The present invention generally relates to enzyme assays. More specifically, the invention is directed to novel assays for acetyltransferases and acetyltransferase substrates.

(2) Description of the Related Art

References Cited

Polevoda and Sherman, 2003, J. Mol. Biol. 325:595-622.

Roth et al., 2001, Annu. Rev. Biochem. 70:81-120.

Acetyltransferases are enzymes that catalyze the transfer of the acetyl moiety from acetyl-CoA to their cognate substrates. These can be small molecule metabolites, antibiotics or proteins. The reaction mechanism can occur in two different ways: the direct transfer of the acetyl group from acetyl-CoA to the substrate, or initial transfer of the acetyl group from acetyl-CoA to an enzyme group on the acetyltransferase to generate the acetyl-enzyme, and subsequent transfer of the acetyl group from the acetyl-enzyme to the substrate. Both of these mechanisms have been demonstrated.

The N-acetylation of proteins by acetyltransferases is a rapidly developing area of cell signaling and regulation. These reactions are important in lifespan, transcriptional regulation, protein stability and drug resistance. Although rapid progress has been made in certain areas, the complete complement of substrates or targets for both procaryotic and eucaryotic acetyltransferases is presently unknown. In particular, bacterial genomes contain many open reading frames identified as members of the GNAT family of N-acetyltransferases (between 18 and 60, depending on the organism).

Improved methods for isolating and identifying acetyltransferases and acetyltransferase substrates are thus needed. The present invention satisfies that need.

SUMMARY OF THE INVENTION

Accordingly, the inventor has discovered that acetyltransferase substrates and acetyltransferases can be identified by combining the acetyltransferase and substrate with a halo-acetyl-CoA or halo-acetyl-pantetheine. The halo-acetyl-CoA or halo-acetyl-pantetheine reacts with the acetyltransferase and substrate to form an acetyl-CoAylated substrate.

Thus, in some embodiments, the invention is directed to methods of identifying an acetyltransferase substrate in a sample. The methods comprise combining the sample with a labeled reagent comprising a thiol, a halo-acetyl-CoA or a halo-acetyl-pantetheine, and an acetyltransferase, under conditions suitable for acetyltransferase enzyme activity, then identifying a substrate that has formed a base-stable covalent bond to the reagent.

In other embodiments, the invention is directed to methods of identifying an acetyltransferase substrate in a sample. The methods comprise combining the sample with a reagent and an acetyltransferase under conditions suitable for acetyltransferase enzyme activity, then identifying a substrate that is associated with the acetyltransferase. In these embodiments, the reagent is a halo-acetyl-CoA or a halo-acetyl-pantetheine, and the acetyltransferase further comprises an affinity tag.

The invention is also directed to methods of localizing acetylation of an acetyltransferase substrate in a cell. The methods comprise combining the cell with a labeled reagent comprising a thiol, and a halo-acetyl-CoA or a halo-acetyl-pantetheine, under conditions suitable for acetyltransferase enzyme activity, then determining the location of the label in the cell.

In further embodiments, the invention is directed to methods of labeling a substrate of an acetyltransferase. The methods comprise combining the substrate with a labeled reagent comprising a thiol, a halo-acetyl-CoA or a halo-acetyl-pantetheine, and an acetyltransferase, under conditions suitable for acetyltransferase enzyme activity.

The invention is additionally directed to methods of assaying an acetyltransferase in a sample, the method comprising combining the sample with a labeled reagent comprising a thiol, a halo-acetyl-CoA or a halo-acetyl-pantetheine, and an acetyltransferase substrate under conditions suitable for acetyltransferase enzyme activity, then determining whether the substrate that has formed a base-stable covalent bond to the reagent, wherein the presence of the base-stable bond of the reagent to the substrate indicates the presence of an acetyltransferase in the sample.

In additional embodiments, the invention is directed to methods of quantifying acetyltransferase activity in a sample. The methods comprise combining the sample with a labeled reagent comprising a thiol, a halo-acetyl-CoA or a halo-acetyl-pantetheine, and an acetyltransferase substrate, under conditions suitable for acetyltransferase enzyme activity, then quantifying the labeled reagent that has formed a base-stable covalent bond to the substrate, wherein the quantity of labeled reagent that has formed a base-stable covalent bond to the substrate is proportional to the acetyltransferase activity in the sample.

The invention is also directed to a halo-acetyl-pantetheine, and a halo-acetyl-CoA-labeled with $^{32}P$, a fluorescent label, or an affinity label.

Additionally, the invention is directed to a halo-acetyl-CoA with a label on the adenine of the CoA, wherein the label is a detectable label or an affinity label.

The invention is further directed to a compound comprising an oligo-His moiety, a thiol, and a detectable label.

DETAILED DESCRIPTION OF THE INVENTION

Figure 1:
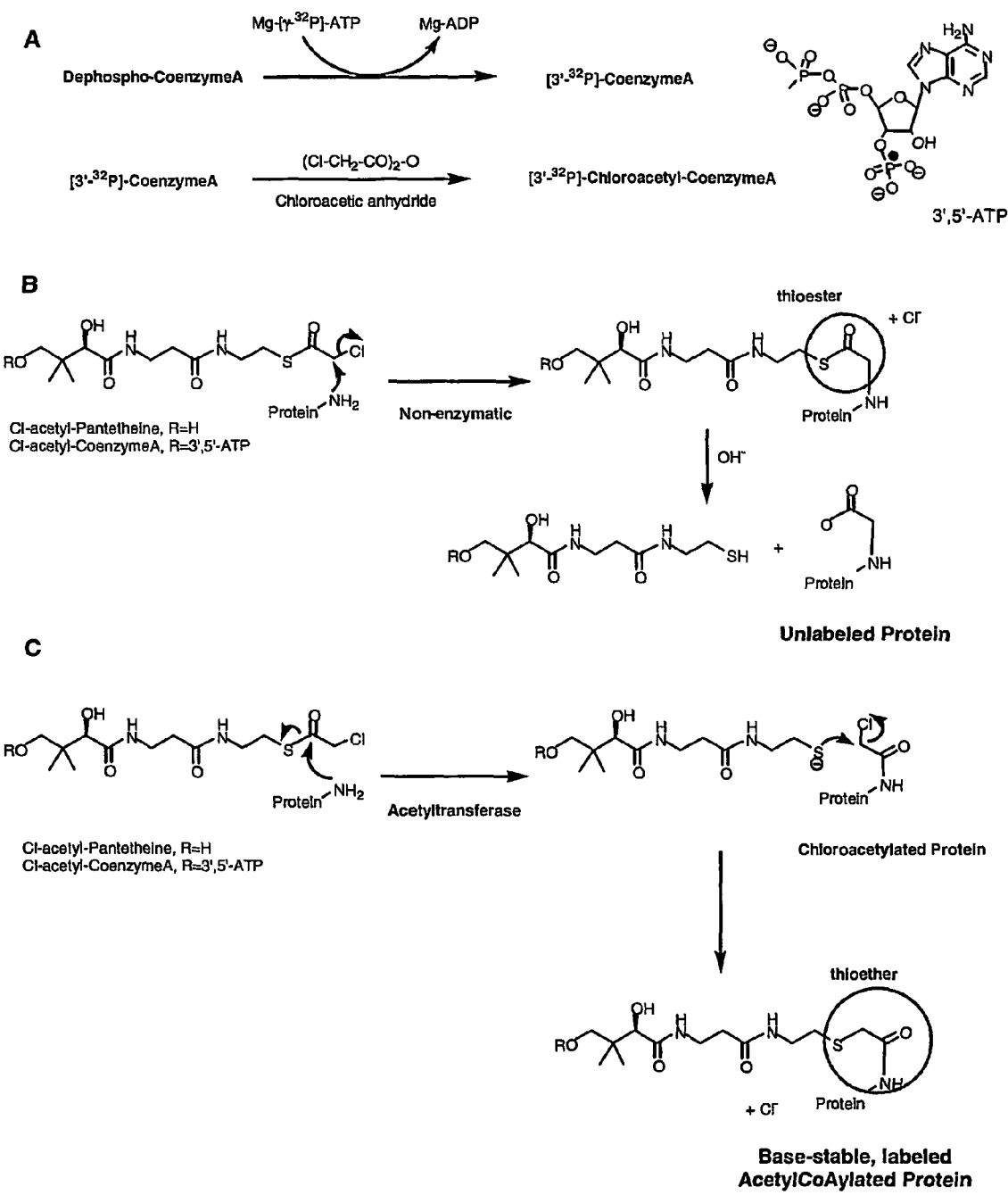
FIG. 1 provides schematics of some chemical reactions useful for the present invention. Panel A provides a reaction scheme for producing $[3'-^{32}P]$-chloroacetyl-CoA. Panel B shows the nonenzymatic reaction of a halo-acetyl-CoA or a halo-acetyl-pantetheine (where the halo moiety is exemplified as a chloro). As indicated, the product of the nonenzymatic reaction is base-labile, and can thus be distinguished from the enzymatic reaction exemplified in Panel C. Panel C shows an example of the acetyltransferase reaction with Cl-acetyl-pantetheine or Cl-acetyl-CoA useful in the present invention.

The present invention is based on the discovery that acetyl-CoA or acetyl-pantetheine that is halogenated on the acetyl methyl moiety ("halo-acetyl-CoA" and "halo-acetyl-pantetheine", respectively) is stably transferred by acetyltransferase to an acetyltransferase substrate in place of the acetyl moiety. The inventor has also discovered that the further addition of another reagent comprising a thiol with the acetyl-CoA or acetyl-pantetheine causes that reagent to be stably covalently bound to the acetyltransferase substrate. These discoveries enable novel methods of identifying, purifying and quantifying acetyltransferases and acetyltransferase substrates. Relevant reactions are provided in FIG. 1. Panel A provides a method of producing a $^{32}$P-labeled chloroacetyl-CoA. Such a labeled reagent, when used in an acetyltransferase reaction, labels the substrate and is therefore useful in identifying, purifying or quantifying acetyltransferases or acetyltransferase substrates. Panel B shows the base-labile nonenzymatic product of a halo-acetyl-CoA or a halo-acetyl-pantetheine with an acetyl group of a protein or small molecule (See Example 1). Since this product is base-labile, this non-enzymatic reaction can be distinguished from the acetyltransferase-mediated conjugation of a halo-acetyl-CoA or a halo-acetyl-pantetheine with an acetyltransferase substrate, exemplified in Panel C of FIG. 1. As shown in that Panel, and without being bound by the particular mechanism shown, the mechanism is believed to proceed as follows. The acetyltransferase causes the initial transfer of the haloacetyl group (here, the chloroacetyl group) to the substrate. The close proximity of the nucleophilic thiol of the CoA results in the attack of the thiol of CoA on the carbon atom to which the halogen (here, chlorine) is bound. This chemistry is well precedented, since α-halo-ketones are known to react with nucleophiles. The attack on the α-halo-ketone releases the halogen (here, chlorine) ion and generates a stable thioether linkage, as well as a stable amide linkage generated in the first step. When the halo-acetyl-CoA is labeled, for example with $^{32}$P (as shown in FIG. 1), the acetyltransferase substrate will become labeled, creating a convenient tag for identifying or quantifying an acetyltransferase or an acetyltransferase substrate.

As established in Example 2, the enzyme-catalyzed transfer of the haloacetyl group to the acetyltransferase substrate is rapid compared to the subsequent reaction of the CoA with the haloacetylated substrate. This suggested that exogenously added compounds comprising a thiol that can also be labeled would be covalently bound to the substrate, thus labeling the substrate with a reagent other than CoA. Experiments provided in Example 2 establish this to be the case.

Accordingly, in some embodiments, the invention is directed to methods of identifying an acetyltransferase substrate in a sample. The methods comprise combining the sample with a labeled reagent comprising a thiol, a halo-acetyl-CoA or a halo-acetyl-pantetheine, and an acetyltransferase, under conditions suitable for acetyltransferase enzyme activity, then identifying a substrate that has formed a base-stable covalent bond to the reagent.

Since acetyltransferases are known to function using the same general method of transfer of the acetyl group to the substrate, these methods would be expected to be useful with any acetyltransferase, now known or later discovered, including any procaryotic, eucaryotic or archaeal acetyltransferases. Non-limiting examples include histone acetyltransferases such as Gcn5, PCAF, Hat1, Elp3, Hpa2, Esa1, MOF, Sas2, Sas3, MORF, Tip60, Hbo1, P300, CBP, TAFII250, TFIIIC, Nut1, ACTR, and SRC1 (Roth et al., 2001); N-terminal acetyltransferases such as NatA, NatB and NatC (Polevoda and Sherman, 2003); arylamine N-acetyltransferases such as NAT1 and NAT2; aminoglycoside acetyltransferases; chloramphenicol acetyltransferases; choline acetyltransferases; carnitine acetyltransferases; spermine acetyltransferases; and ornithine acetyltransferases. Any substrate of any acetyltransferase is also useful in the present inventions, including proteins, oligopeptides, antibiotics, or small organic molecules less than 500 molecular weight.

As used herein, "halo" includes a chlorine, bromine, fluorine or iodine substitution on the acetyl group methyl moiety of acetyl-CoA or acetyl-pantetheine (see FIG. 1). Additionally, "halo-acetyl-CoA" and a "halo-acetyl-pantetheine" are not narrowly limited to the single unsubstituted species of each form, but encompasses the unsubstituted halo-acetyl-CoA and halo-acetyl-pantetheine as well as any substituted halo-acetyl-CoA and halo-acetyl-pantetheine that would be understood by the skilled artisan to be capable of conjugation to an acetyltransferase substrate by an acetyltransferase. Non-limiting examples of such substitutions include any molecule up to about 500 mw conjugated to the adenine group of the halo-acetyl-CoA. In the three-dimensional structure of bacterial and eucaryotic acetyltransferases, CoA is bound in a way that the adenine ring makes few interactions with acetyltransferase and is essentially completely solvent exposed. Therefore, essentially any substitution on the adenine group would not be expected to interfere with the enzymatic action.

In these embodiments, the labeled reagent can be the halo-acetyl-CoA or halo-acetyl-pantetheine, or it can be an additional reagent comprising a thiol. Examples of the latter include a thiol-containing fluorophore, for example a fluorophore modified with aminoethanethiol. See, e.g., aminoethanethiolated-TAMRA, the structure of which is provided in FIG. 3. These reagents can also comprise any other moiety, for example an oligo-histidine tag ("oligo-His") such as His6, since those tags can be readily incorporated into an acetyltransferase by molecular biological methods. As is well known, oligo-His tagged proteins are easily purified with Ni columns. See Example 2.

In preferred embodiments, the halo-acetyl-CoA or halo-acetyl-pantetheine is a halo-acetyl-CoA, since acetyl-CoA is the natural acetyl group contributor in acetyltransferase action. Since the halo-acetyl-CoA is exemplified herein (see Examples) as chloroacetyl-CoA and bromoacetyl-CoA, those compounds are particularly preferred. However, fluoroacetyl-CoA and iodoacetyl-CoA would also be expected to also be useful in these methods. Selection of the most useful halo-acetyl-CoA for any particular purpose could be made by the skilled artisan without undue experimentation.

In many embodiments, the halo-acetyl-CoA or halo-acetyl-pantetheine reagent preferably further comprises a detectable label or an affinity label, for example to easily detect and/or purify the acetyltransferase substrates binding the reagent. The invention is not narrowly limited to any particular detectable or affinity label, and the skilled artisan could select and utilize an appropriate label for any particular purpose without undue experimentation. Nonlimiting examples of useful labels include radioactive labels (e.g., $^{32}$P, $^{14}$C, $^{3}$H), fluorescent labels, and affinity labels such as biotin. Where the reagent is a halo-acetyl-CoA, a preferred label is $^{32}$P (see FIG. 1 and Example 1 for methods of synthesizing and utilizing $^{32}$P-halo-acetyl-CoA).

The present methods are useful with any sample comprising an acetyltransferase substrate. It is envisioned that the methods would be most useful where the sample is an extract of a cell.

The identification of the substrate in these methods could be by any appropriate means, including, for example, gel electrophoresis (especially useful when the substrate is a protein—See Examples), mass spectroscopy or nuclear magnetic resonance, or combinations of these methods.

Acetyltransferases are known to have a very high steady-state affinity for acetyl-CoA. Since the present invention provides for the covalent binding of acetyl-CoA or acetyl-pantetheine to the acetyltransferase substrate, the acetyltransferase would be expected to bind to the acetyl-CoA or acetyl-pantetheine that is covalently bound to the substrate. This suggests methods of identifying an acetyltransferase substrate in a sample. The methods comprise combining the sample with a reagent and an acetyltransferase under conditions suitable for acetyltransferase enzyme activity, then identifying a substrate that is associated with the acetyltransferase. In these embodiments, the reagent is a halo-acetyl-CoA or a halo-acetyl-pantetheine, and the acetyltransferase further comprises an affinity tag. The affinity tag is used to purify the acetyltransferase-acetyl-CoA-substrate complex. The substrate on the purified complex is then identified by standard methods.

Any affinity tag that can be used to purify the complex can be used. In preferred embodiments, the affinity tag is an oligo-His tag.

Since a labeled halo-acetyl-CoA or halo-acetyl-pantetheine, or another labeled thiolated compound added with a halo-acetyl-CoA or halo-acetyl-pantetheine, covalently binds to acetyltransferase substrates, the location of the labeled substrates can be used to determine the location of the acetyltransferase activity in the cell. Such methods are useful for determining, e.g., whether a histone acetyltransferase also acetylates proteins located outside the nucleus, etc. Thus, the invention is additionally directed to methods of localizing acetylation of an acetyltransferase substrate in a cell. The methods comprise combining the cell with a labeled reagent comprising a thiol, and a halo-acetyl-CoA or a halo-acetyl-pantetheine, under conditions suitable for acetyltransferase enzyme activity, then determining the location of the label in the cell.

In these methods, the label is preferably a detectable label such as a radioactive label, e.g., $^{32}$P, or a fluorescent label. The label can also be an affinity label such as biotin, which can be detected, e.g., using avidin-labeled detectable enzyme such as peroxidase or alkaline phosphatase, using well-known methods.

The location of the label in the cell can be determined by any appropriate method, e.g., light microscopy, autoradiography, or fluorescence microscopy. The most appropriate method for any particular application can be selected without undue experimentation.

These methods could be used with any procaryotic, archaeal, or eucaryotic cell. It would be expected to be most useful for eucaryotic cells, since they are known to be more compartmentalized than procaryotic or archaeal cells, and would therefore be expected to show more prominent localization of acetyltransferase activity than archaeal or procaryotic cells.

Since halo-acetyl-CoA or halo-acetyl-pantetheine, or another labeled thiolated compound added with a halo-acetyl-CoA or halo-acetyl-pantetheine, covalently bind stably to acetyltransferase substrates, the reagents can be used to label acetyltransferase substrates. Thus, in additional embodiments, the invention is directed to methods of labeling a substrate of an acetyltransferase. The methods comprise combining the substrate with a labeled reagent comprising a thiol, a halo-acetyl-CoA or a halo-acetyl-pantetheine, and an acetyltransferase, under conditions suitable for acetyltransferase enzyme activity. These methods could be used with any acetyltransferase substrate, although it would be expected to be most useful with protein acetyltransferase substrates.

As with the methods described above, these methods could be used with any acetyltransferase, including histone acetyltransferases, N-terminal acetyltransferases, arylamine N-acetyltransferases, aminoglycoside acetyltransferases, chloramphenicol acetyltransferases, choline acetyltransferases, carnitine acetyltransferases, spermine acetyltransferases, and ornithine acetyltransferases. Also as with previously described methods, the labeled reagent can be the halo-acetyl-CoA or halo-acetyl-pantetheine, or it can be an additional reagent comprising a thiol, for example a fluorophore modified with aminoethanethiol. These reagents can also comprise any other moiety, for example an oligo-His tag.

In preferred embodiments, the halo-acetyl-CoA or halo-acetyl-pantetheine is a halo-acetyl-CoA, most preferably chloroacetyl-CoA or bromoacetyl-CoA. However, fluoroacetyl-CoA and iodoacetyl-CoA would also be expected to also be useful in these methods.

These methods could be used with a purified substrate and acetyltransferase, or with either or both in an impure state, e.g., in a cellular extract, a food, or an environmental sample (see, e.g., Example 2).

The present invention is also directed to methods of assaying an acetyltransferase in a sample. The methods comprise combining the sample with a labeled reagent comprising a thiol, a halo-acetyl-CoA or a halo-acetyl-pantetheine, and an acetyltransferase substrate under conditions suitable for acetyltransferase enzyme activity, then determining whether the substrate has formed a base-stable covalent bond to the reagent, where the presence of the base-stable bond of the reagent to the substrate indicates the presence of an acetyltransferase in the sample.

These methods are not limited to any particular type of sample, and could include, for example, a food or an environmental sample. It would be expected that these methods would be particularly useful where the sample is an extract of a cell. Cellular extracts include those from archaeal, procaryotic, or eucaryotic cells. See Example 2.

As with the methods described above, these methods could be used with any acetyltransferase, including histone acetyltransferases, N-terminal acetyltransferases, arylamine N-acetyltransferases, aminoglycoside acetyltransferases, chloramphenicol acetyltransferases, choline acetyltransferases, carnitine acetyltransferases, spermine acetyltransferases, and ornithine acetyltransferases. Also as with previously described methods, the labeled reagent can be the halo-acetyl-CoA or halo-acetyl-pantetheine, or it can be an additional reagent comprising a thiol, for example a fluorophore modified with aminoethanethiol. These reagents can also comprise any other moiety, for example an oligo-His tag.

In preferred embodiments, the halo-acetyl-CoA or halo-acetyl-pantetheine is a halo-acetyl-CoA, most preferably chloroacetyl-CoA or bromoacetyl-CoA. However, fluoroacetyl-CoA and iodoacetyl-CoA would also be expected to also be useful in these methods.

These methods are useful with any acetyltransferase substrate, including proteins, e.g., histones, antibiotics, and substrates that are metabolites less than 500 molecular weight.

The present invention is also directed to methods of quantifying acetyltransferase activity in a sample. The methods comprise combining the sample with a labeled reagent comprising a thiol, a halo-acetyl-CoA or a halo-acetyl-pantetheine, and an acetyltransferase substrate, under conditions suitable for acetyltransferase enzyme activity, then quantifying the labeled reagent that has formed a base-stable covalent bond to the substrate, where the quantity of labeled reagent that has formed a base-stable covalent bond to the substrate is proportional to the acetyltransferase activity in the sample.

These methods are not limited to any particular type of sample, and could include, for example, a food or an environmental sample. It would be expected that these methods would be particularly useful where the sample is an extract of a cell. Cellular extracts include those from archaeal, procaryotic, or eucaryotic cells.

As with the methods described above, these methods could be used with any acetyltransferase, including histone acetyltransferases, N-terminal acetyltransferases, arylamine N-acetyltransferases, aminoglycoside acetyltransferases, chloramphenicol acetyltransferases, choline acetyltransferases, carnitine acetyltransferases, spermine acetyltransferases, and ornithine acetyltransferases. Also as with previously described methods, the labeled reagent can be the halo-acetyl-CoA or halo-acetyl-pantetheine, or it can be an additional reagent comprising a thiol, for example a fluorophore modified with aminoethanethiol. These reagents can also comprise any other moiety, for example an oligo-His tag.

In preferred embodiments, the halo-acetyl-CoA or halo-acetyl-pantetheine is a halo-acetyl-CoA, most preferably chloroacetyl-CoA or bromoacetyl-CoA. However, fluoroacetyl-CoA and iodoacetyl-CoA would also be expected to also be useful in these methods.

These methods are useful with any acetyltransferase substrate, including proteins, e.g., histones, antibiotics, and substrates that are metabolites less than 500 molecular weight.

The skilled artisan could quantify the labeled reagent without undue experimentation using known methods for quantifying any label that would be utilized.

In additional embodiments, the present invention is directed to a halo-acetyl-pantetheine, which is novel, and rendered useful by the invention methods described above. The halo group of the invention halo-acetyl-pantetheine can be a chloro-, fluoro-, bromo-, or iodo-group.

In related embodiments, the invention is directed to a halo-acetyl-pantetheine as described immediately above, where the halo-acetyl-pantetheine has a detectable label or an affinity label. Nonlimiting examples of the label include radioactive labels, e.g., $^{32}P$ or $^{14}C$, a fluorescent label, or the affinity label biotin.

In other related embodiments, the invention is directed to a halo-acetyl-CoA labeled with $^{32}P$, a fluorescent label, or an affinity label (e.g., biotin). These compounds were previously unknown, and are made useful by the methods described above. These compounds encompass any halo group, i.e., chloro-, fluoro-, bromo-, or iodo-.

The invention is additionally directed to a halo-acetyl-CoA with a label on the adenine of the CoA, where the label is a detectable label or an affinity label. As with the other invention compounds described above, these compounds were previously unknown and are made useful by the novel invention methods. The detectable or affinity labels include those that have been previously described, e.g., radioactive labels (for example $^{32}P$, $^{14}C$, or $^{3}H$), any known fluorescent label, or any affinity label, e.g., biotin.

The invention is further directed to a compound comprising an oligo-His moiety, a thiol, and a detectable label. The detectable label can be any of those described above, e.g., a radioactive label, a fluorescent label, or any affinity label. In other aspects of these embodiments, the compound is an acetyltransferase substrate.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

An Assay for Acetyltransferases and Acetyltransferase Substrates

This Example provides some methods that can be used to assay for acetyltransferases and acetyltransferase substrates.

There are only three bacterial acetyltransferases whose substrates are known to be bacterial proteins. These are the rimI-, rimJ- and rimL-encoded a-N-acetyltransferases whose physiological substrates are the ribosomal proteins S5, S18 and L12. These three ribosomal proteins are post-translationally modified by the removal of the initiating formyl-methionine amino acid, and subsequently α-N-acetylated on their N-terminal alanine or serine residues. We have cloned, expressed and purified both the *S. enterica* RimL acetyltransferase and the L12 substrate. RimL is isolated in a highly a-N-acetylated form (>95%) while L12 is purified as a mixture of a-N-acetylated and non-acetylated forms (~25% acetylated, 75% non-acetylated).

Materials and Methods

Synthesis of [3'-$^{32}P$]Chloroacetyl-CoenzymeA. 60 µCi of [γ-$^{32}P$]-ATP was added to 1 µmole dephosphoCoA, 10 µmoles MgCl$_2$ and 3 µmoles of recombinant *E. coli* dephosphoCoA kinase in 50 mM Tris, pH 7.5. After ten min at 25° C., 0.3 µmole of ATP was added. After an additional 20 minutes at 25° C. degrees, 1.5 µmoles of phosphoenolpyruvate, 8 units of pyruvate kinase and 2 more nmoles of dephosphoCoA kinase were added. The reaction mixture was incubated an additional 60 min at 37° C. Enzymes were removed by passage through an Amicon 10 kilodalton molecular weight cut-off centrifugal filter, and the solution was lyophilized. The lyophilized powder was dissolved in 0.5 ml of 30 mM Tris buffer, pH 7.8 in 50% aqueous tetrahydrofuran. 0.2 ml of a solution containing 1.7 µmoles of chloroacetic acid and 2.3 µmoles of carbonyldiimidazole in tetrahydrofuran was added. The reaction was allowed to proceed for 2 h at room temperature, at which time, the thiol of CoA could not be detected by reaction with DTNB. This mixture was lyophilized.

Reaction of RimL and L12 with Chloroacetyl CoenzymeA. Four tubes were prepared that contained 1) 4 µM *Salmonella enterica* RimL, 2) 10 µM *Salmonella enterica* L12, 3) 4 µM *Salmonella enterica* RimL and 10 µM *Salmonella enterica* L12 and 4) 3 µM bovine serum albumin (BSA). 10 µl of a solution containing 75 mM Tris, pH 7.3 and 3.6 nmoles of [3'-$^{32}$P]chloroacetylCoA (0.2 µCi) was added to each tube (80 µM final concentration), and allowed to stand at room temperature for 90 min. The contents of each tube were equally divided, and half of the reaction mixture was adjusted to pH 13 by the addition of 200 mM CHES buffer, pH 13.5. These mixtures were incubated at 100° C. for two min. The solution pH was readjusted to pH 7-8 by the addition of 1N HCl. SDS-PAGE loading buffer was added to 5 µl aliquots of both the untreated and treated samples, and then heated at 100° C. for 2 min. One µl aliquots were analyzed on 10-15% acrylamide gels using the Pharmacia PhastSystem. The gel was stained with Coomassie Blue, destained and dried. The radioactivity was determined using a PhosphoImager system.

Results

Figure 2:
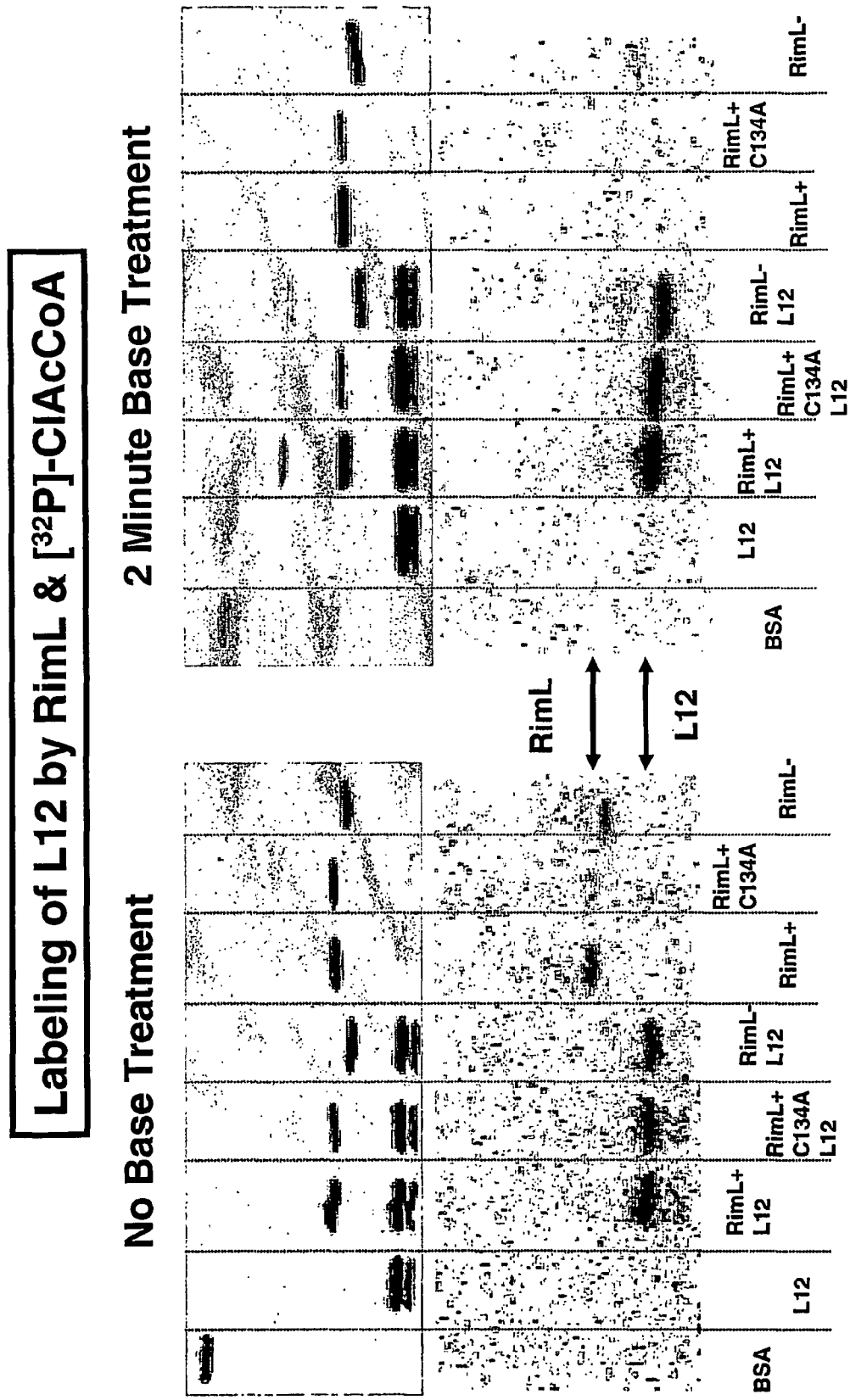
FIG. 2 is a photograph of a Coomassie-stained (top panel) and an autoradiograph (bottom panel) of an SDS-PAGE gel of the products of the reactions the incubation of RimL acetyltransferase (RimL) and its L12 substrate (L12) with [3'-$^{32}$P] chloro-acetyl-CoA, in some cases further treating the reaction products with a pH 13 buffer (OH—). The BSA treatments were controls. These results validate the reaction mechanisms provided in FIG. 1.

The results of these experiments are provided in FIG. 2. Incubation of purified RimL acetyltransferase and its L12 substrate with [$^{14}$C-acetyl]-AcCoA results in labeling of L12. Incubation of these purified proteins with [3'-$^{32}$P]-ClAcCoA causes both RimL and L12 to become radiolabeled, as shown in the autoradiogram of the SDS-PAGE gel in FIG. 2 (Lane 4). However, pre-treatment of this sample with base (pH 12, 100° C., 5 minutes) followed by SDS-PAGE results in the nearly quantitative removal of the label from RimL, but nearly quantitative retention of the label by L12 (Lane 3). The small amount of retained label on RimL is very likely to represent the self-α-N-acetylation of the small amount of non-acetylated RimL originally present, a reaction that we have previously demonstrated. No reaction was observed with either L12 alone or BSA. These results validate the proposed reactions provided in FIG. 1.

EXAMPLE 2

Further Characterization of the Assay

Figure 4:
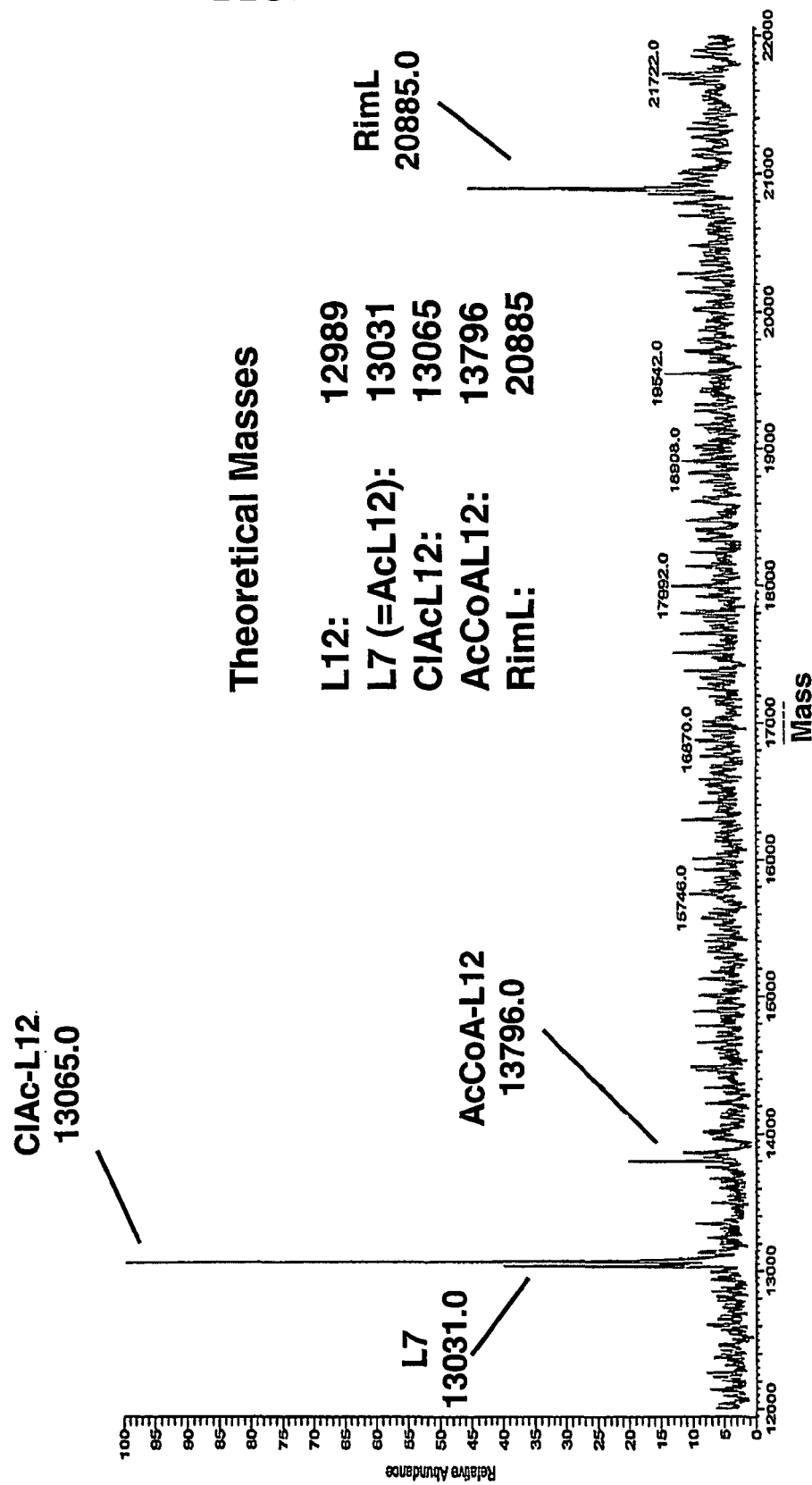
FIG. 4 shows a mass spectrum of RimL-catalyzed acetyl-CoAylation of L12, as described in Example 2.

The introduction of the halogen allows for a thiol, either the product thiol of CoA or potentially an exogenously added thiol-containing compound, to react to generate a covalent and stable linkage. In order to determine the efficiency of the product thiol of CoA to react with the haloacetylated substrate, we performed a mass spectrometric identification of the products of the RimL-catalyzed chloroacetylation of the bacterial L12 protein. These results are shown in FIG. 4.

Figure 3:
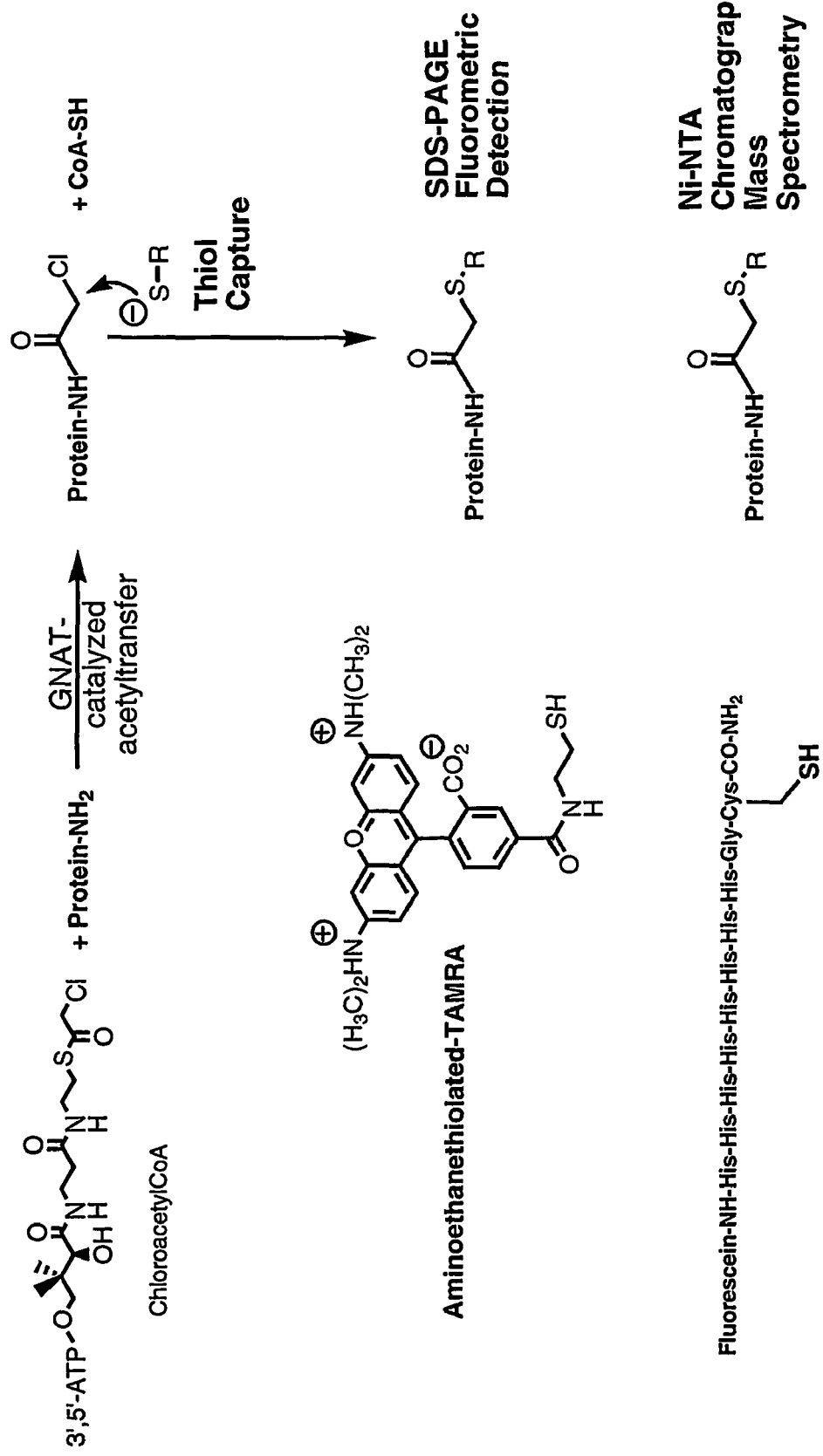
FIG. 3 shows schematics of chemical reactions and structures of compounds evaluated in Example 2.
Figure 5:
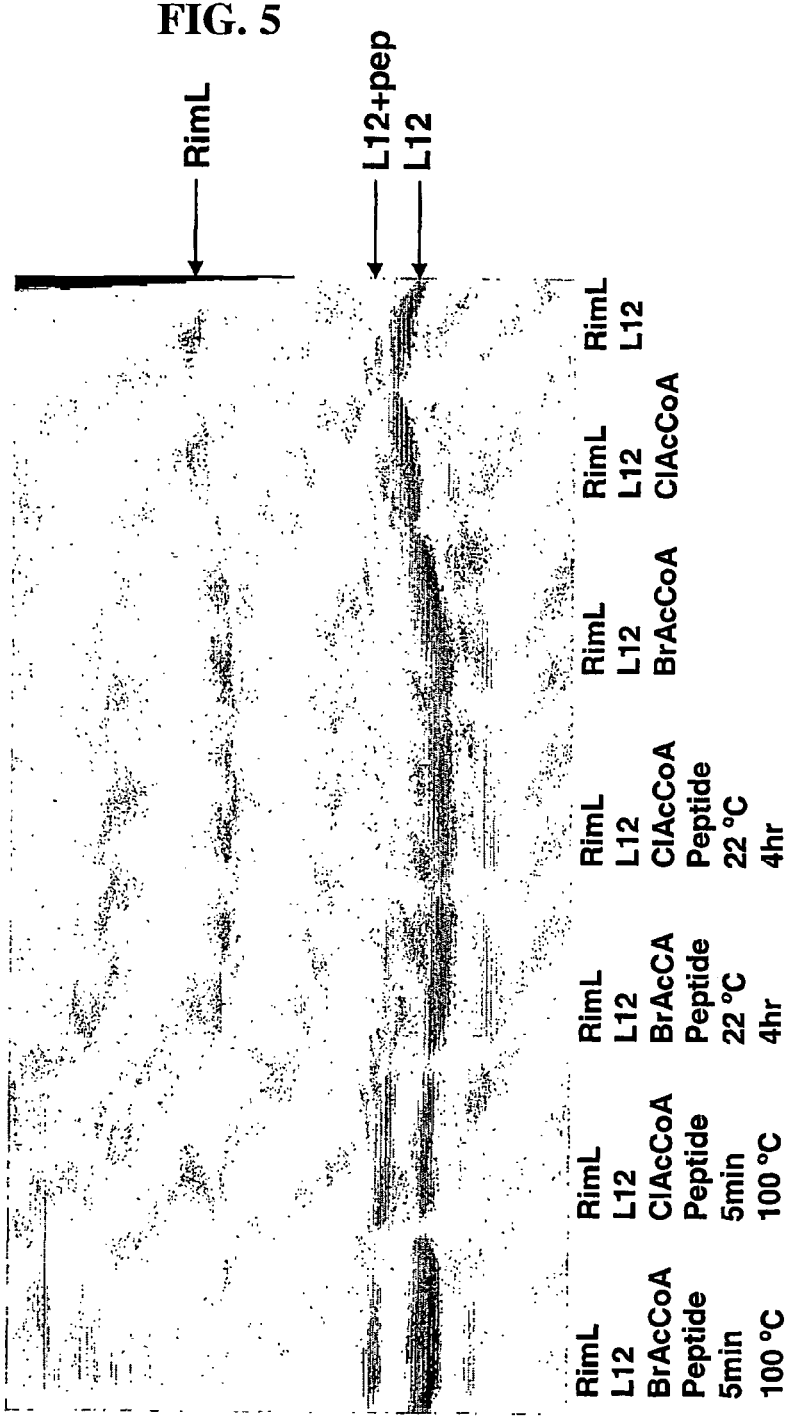
FIG. 5 is a Coomassie-stained SDS-PAGE gel of RimL-catalyzed acetylCoAylation of L12 using chloroacetyl-CoA or bromoacetyl-CoA.

It is apparent that after 10-minute incubations, that no L12 can be observed and that the major product is the chloroacetylated L12 (m/z=13065). Only small amounts of the acetyl-CoAylated L12 is observed. This suggested that exogenously added thiol-containing compounds might compete with CoA effectively, and increase the sensitivity of the method. Results for two compound types will be described. The first are modified peptides that contain a His8 sequence to allow for affinity purification on Ni affinity columns, an N-terminal fluorophore, and a C-terminal cysteine residue that will serve as the nucleophile. The second are fluorophores that are modified with aminoethanethiol to introduce the thiol capture reagent (FIG. 3). RimL will catalyze the reaction of ClAcCoA and L12 to generate the ClAc-L12, and reaction with the peptide HHHHGGC generates HHHHHGGC-Ac-L12 that can be observed on SDS-PAGE as a band migrating at a higher molecular weight (FIG. 5).

Figure 6:
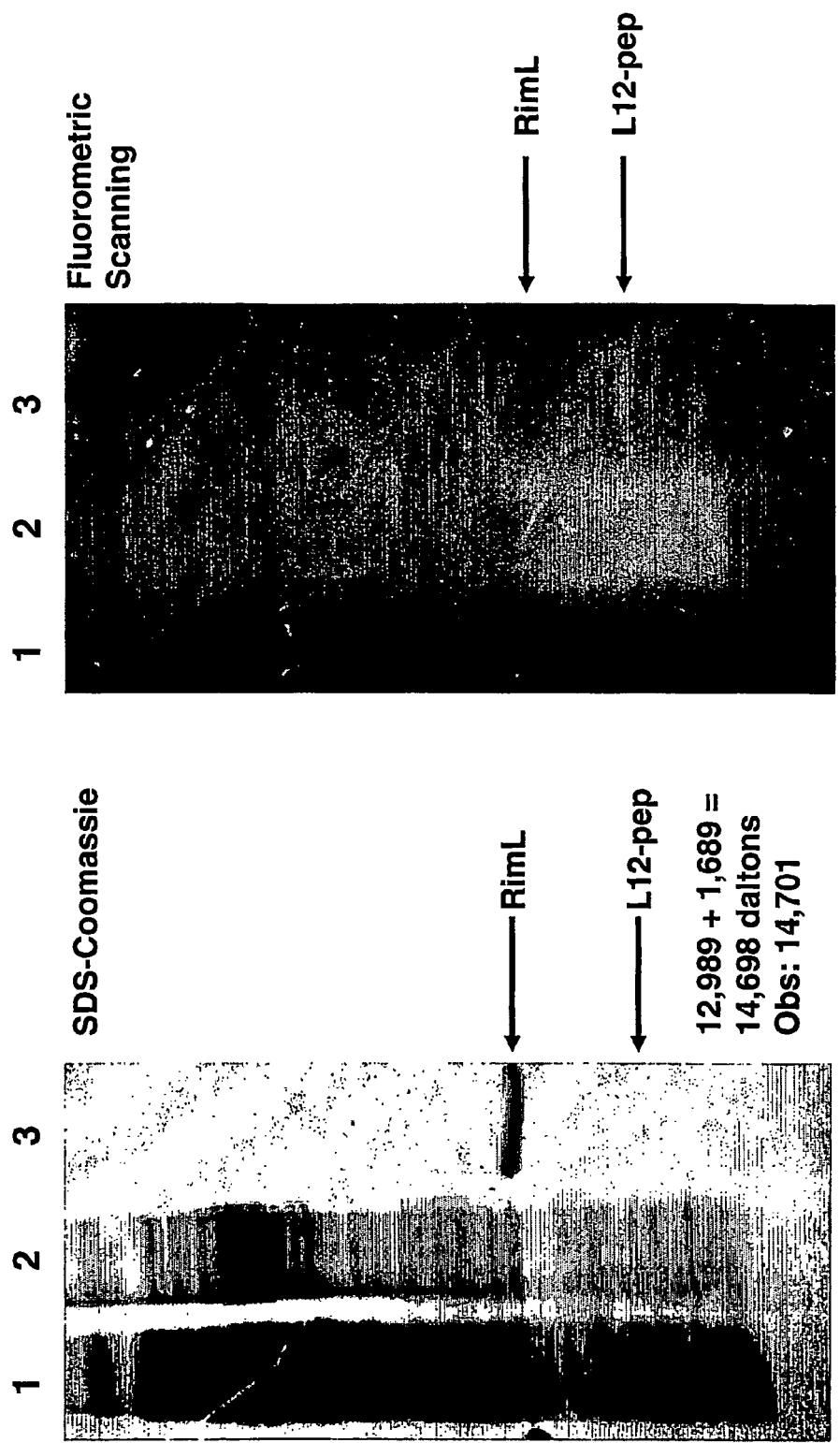
FIG. 6 is a Coomassie-stained (left) and fluorometrically-scanned (right) SDS-PAGE gel of a *Salmonelle enterica* extract of fluorescent and His6-tagged RimL-catalyzed chloroacetylCoAylation of L12 before or after Ni-NTA purification.

To answer the question of whether this reagent and method can be applied to in vivo systems, we used a nonapeptide containing 8 histidine residues and a C-terminal cysteine residue to which a fluorescein fluorophore was attached at the N-terminus. Crude cell lysates of *Salmonelle enterica* (FIG. 6, lane 1), the organism from which both RimL and L12 were cloned, were added to a reaction mixture containing RimL and ClAcCoA. After ten minutes, the fluorogenic peptide was added to the reaction mixture and the entire mixture was applied to a Ni-NTA affinity resin. After extensive washing, 500 mM imidazole was added to elute those proteins containing a His6-8 tag. As shown in lane 3 of FIG. 6, the His6-tagged RimL was clearly visible, while an extremely faint band was observed in this Coomassie-stained gel. Before Coomassie staining, this gel was visualized by scanning the gel using fluorescence. As one can see in lane 3, only the band corresponding to the fluorescently labeled L12 is observed. This indicates that "substrate profiling" using this method and expressed GNAT enzymes will allow for the identification of protein, and small molecule, substrates.

Figure 7:
FIG. 7 is a Coomassie-stained (left) and fluorometrically-scanned (right) SDS-PAGE gel of the result of the incubation of Hat1, histones, a thiolated fluorophore (aminoethanethiolated-TAMRA—see FIG. 3) and chloroacetyl-CoA.
Figure 7:
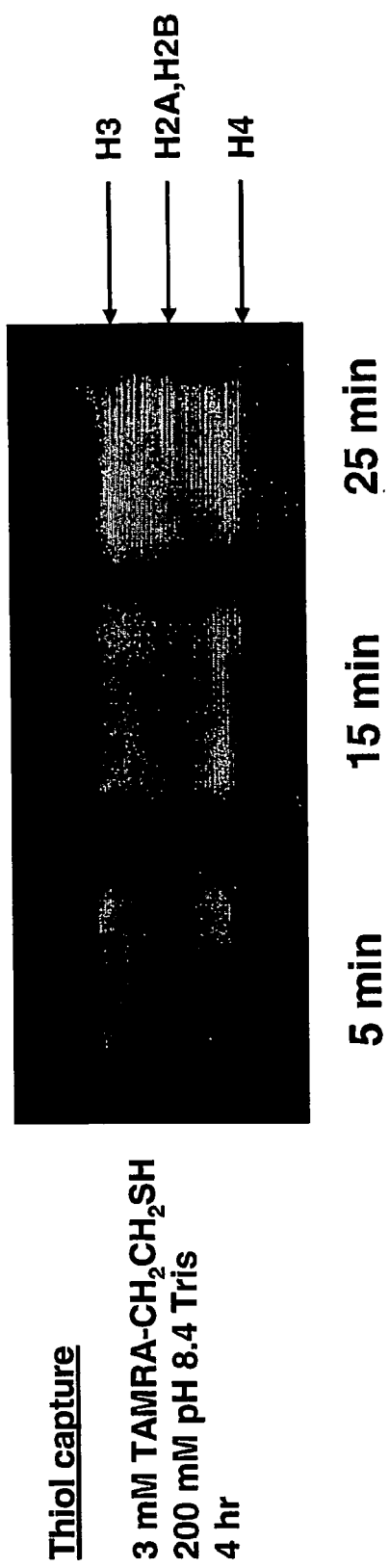

Finally, to assess the breadth of the reagent and methods utility, we used yeast Hat1 histone acetyltransferase and a mixture of purified histone proteins. After incubation of Hat1, fluorescent-labeled histones, ClAcCoA and the thiolated fluorophore aminoethanethiolated-TAMRA, the histones were covalently labeled and could be visualized fluorometrically, as shown in FIG. 7.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of identifying an acetyltransferase substrate in a sample, the method comprising the steps of:
   (a) contacting the sample with
      (i) a reagent comprising an aminoethanethiol, a halo-acetyl-CoA or a halo-acetyl-pantetheine, and
      (ii) an acetyltransferase,
   under conditions suitable for acetyltransferase enzyme activity, and
   (b) identifying a substrate that has formed a base-stable covalent bond to the reagent, wherein the reagent is labeled with a label and/or the acetyltransferase is labeled with an affinity tag, and the substrate is the acetyltransferase substrate.

2. The method of claim 1, wherein the reagent is the halo-acetyl-CoA labeled with a label.

3. The method of claim 1, wherein the reagent is the halo-acetyl-pantetheine labeled with a label.

4. The method of claim 1, wherein the reagent is the aminoethanethiol labeled with a label.

5. The method of claim 1, wherein the reagent comprises the halo-acetyl-CoA and the aminoethanethiol, wherein either the halo-acetyl-CoA or the aminoethanethiol is labeled with a label.

6. The method of claim 1, wherein the reagent comprises the halo-pantetheine CoA and the aminoethanethiol, wherein either the halo-acetyl-CoA or the aminoethanethiol is labeled with a label.

7. The method of claim 2, wherein the halo-acetyl-CoA is a chloroacetyl-CoA.

8. The method of claim 2, wherein the halo-acetyl-CoA is a bromoacetyl-CoA.

9. The method of claim 2, wherein the halo-acetyl-CoA is a fluoroacetyl-CoA or an iodoacetyl-CoA.

10. The method of claim 4, wherein the aminoethanethiol is labeled with a fluorophore.

11. The method of claim 1, wherein the label is radioactive.

12. The method of claim 11, wherein the radioactive label is $^{32}P$.

13. The method of claim 1, wherein the label is fluorescent.

14. The method of claim 1, wherein the label is an affinity label.

15. The method of claim 14, wherein the affinity label is biotin.

16. The method of claim 1, wherein the acetyltransferase is labeled with an affinity tag.

17. The method of claim 16, wherein the affinity tag is an oligo-His tag.

18. The method of claim 1, wherein the acetyltransferase is selected from the group consisting of a histone acetyltransferase, an N-terminal acetyltransferase, an arylamine N-acetyltransferase, an aminoglycoside acetyltransferase, chloramphenicol acetyltransferase, choline acetyltransferase, carnitine acetyltransferase, spermine acetyltransferase, and ornithine acetyltransferase.

* * * * *

UNITED STATES PATENT AND TRADEMARK OFFICE
CERTIFICATE OF CORRECTION

| | | |
|---|---|---|
| PATENT NO. | : 7,745,163 B2 | Page 1 of 1 |
| APPLICATION NO. | : 10/574307 | |
| DATED | : June 29, 2010 | |
| INVENTOR(S) | : John S. Blanchard | |

It is certified that error appears in the above-identified patent and that said Letters Patent is hereby corrected as shown below:

In the Specification

Column 1, lines 12-17, should read:

-- STATEMENT OF GOVERNMENT SUPPORT

This invention was made with government support under grant number AA133696 awarded by the National Institutes of Health. The government has certain rights in the invention. --

Signed and Sealed this
Twenty-ninth Day of December, 2015

Michelle K. Lee
*Director of the United States Patent and Trademark Office*